(12) United States Patent
Dixon et al.

(10) Patent No.: US 7,361,623 B2
(45) Date of Patent: Apr. 22, 2008

(54) TRIMERISATION AND OLIGOMERISATION OF OLEFINS USING A CHROMIUM BASED CATALYST

(75) Inventors: John Thomas Dixon, Vanderbijlpark (ZA); Jacobus Johannes Cronje Grove, Johannesburg (ZA); Peter Wasserscheid, Cologne (DE); David Shane McGuinness, Crossgate (GB); Fiona Millicent Hess, Vaalpark (ZA); Hulisani Maumela, Johannesburg (ZA); David Hedley Morgan, Johannesburg (ZA); Annette Bollman, Henley-on-Klip (ZA)

(73) Assignee: Sasol Technology (Pty) Ltd., Johannesburg (ZA)

( * ) Notice: Subject to any disclaimer, the term of this patent is extended or adjusted under 35 U.S.C. 154(b) by 0 days.

(21) Appl. No.: 10/499,244

(22) PCT Filed: Dec. 19, 2002

(86) PCT No.: PCT/ZA02/00217

§ 371 (c)(1),
(2), (4) Date: Dec. 29, 2004

(87) PCT Pub. No.: WO03/053891

PCT Pub. Date: Jul. 3, 2003

(65) Prior Publication Data
US 2005/0119516 A1    Jun. 2, 2005

(30) Foreign Application Priority Data
Dec. 20, 2001    (ZA)    .................... 2001/10435

(51) Int. Cl.
B01J 31/00    (2006.01)
C08F 4/02     (2006.01)
C08F 4/60     (2006.01)
C07C 5/23     (2006.01)

(52) U.S. Cl. ............... 502/150; 502/103; 502/162; 502/167; 585/665

(58) Field of Classification Search ............ 502/150, 502/162, 167, 103; 585/665
See application file for complete search history.

(56) References Cited

U.S. PATENT DOCUMENTS 5,223,631 A    6/1993    Cheng et al. ............... 549/533

(Continued)

FOREIGN PATENT DOCUMENTS

EP    0 537 609    4/1993

(Continued)

OTHER PUBLICATIONS

Hessler, A. et al., "Wasserlösliche Phosphane VII Synthese, Koordinationschemie und Templatereaktionen PH-funktioneller Bis(phosphinoethyl)amine", *Journal of Organometallic Chemistry*, vol. 553, pp. 39-52, 1998; Xp-002237140.

(Continued)

*Primary Examiner*—Helene Klemanski
(74) *Attorney, Agent, or Firm*—Occhiuti Rohlicek & Tsao LLP

(57) ABSTRACT

The invention provides a mixed heteroatomic ligand for an oligomerisation of olefins catalyst, which ligand includes at least three heteroatoms, of which at least one heteroatom is nitrogen and at least two heteroatoms are not the same. The invention also provides a multidentate mixed heroatomic ligand for an oligomerization of olefins catalyst, which ligand includes at least three heteroatoms. At least one heteroatom may be nitrogen and at least 2 heteroatoms may not be the same.

30 Claims, 1 Drawing Sheet

U.S. PATENT DOCUMENTS

Figure 1:
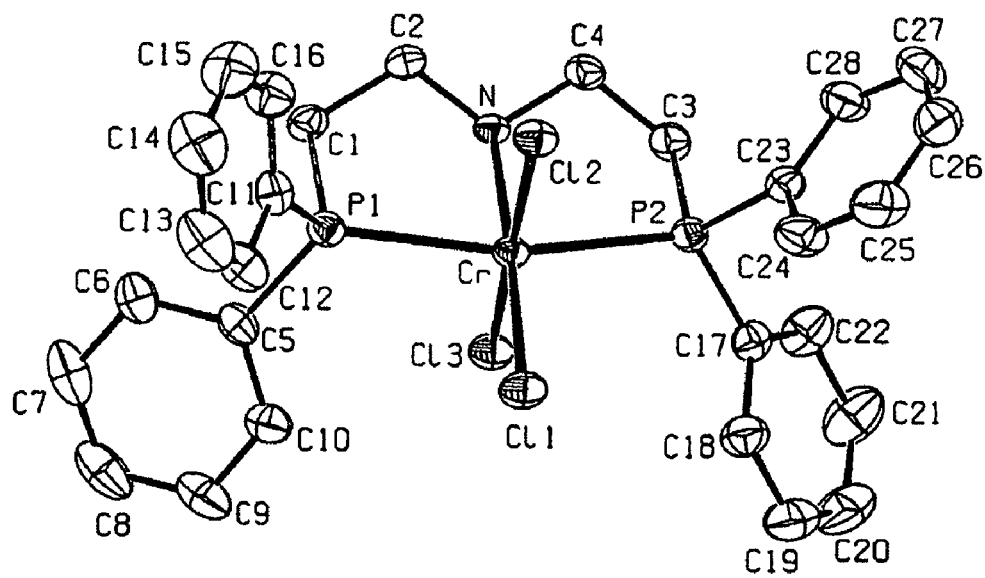

| | | | |
|---|---|---|---|
| 5,550,305 A * | 8/1996 | Wu | 585/513 |
| 5,621,062 A | 4/1997 | Castellucci et al. | 528/30 |
| 5,744,677 A * | 4/1998 | Wu | 585/512 |
| 5,811,618 A | 9/1998 | Wu | |
| 5,968,866 A * | 10/1999 | Wu | 502/155 |
| 6,337,297 B1 * | 1/2002 | Mimura et al. | 502/117 |
| 6,362,309 B1 | 3/2002 | Lund et al. | 528/373 |
| 6,384,282 B2 * | 5/2002 | Hartwig et al. | 564/485 |
| 6,610,805 B1 | 8/2003 | Guram et al. | 526/172 |
| 6,838,563 B2 | 1/2005 | Mihan et al. | 546/10 |
| 6,863,781 B2 * | 3/2005 | Nocera et al. | 204/157.52 |
| 6,900,152 B2 * | 5/2005 | Yoshida et al. | 502/103 |
| 6,911,516 B1 | 6/2005 | Mihan et al. | 526/348 |
| 6,924,248 B2 | 8/2005 | Mihan et al. | 502/132 |
| 6,943,224 B2 * | 9/2005 | Shih | 526/113 |
| 2003/0149198 A1 | 8/2003 | Small et al. | 525/115 |
| 2005/0070425 A1 | 3/2005 | Biagini et al. | 502/117 |

FOREIGN PATENT DOCUMENTS

| | | |
|---|---|---|
| EP | 0 949 265 | 10/1999 |
| JP | 2002241382 A | 8/2002 |
| WO | WO98/25939 | 6/1998 |
| WO | WO 01/83447 | 11/2001 |
| WO | WO 02/04119 | 1/2002 |

OTHER PUBLICATIONS

Hii, King Kouk M. and Thorton-Pett, M., "Syntheses and Properties of Palladium Complexes Containing Phosphorus-Nitrogen-Phosphorus Ligands with a Tunable Hemilabile Site", *Organometallics*, vol. 18, pp. 1887-1896, 1999.

Nuzzo, R.G. et al., "Synthesis of Functional Chelating Diphosphines Containing the Bis[2-(diphenylphosphino)ethyl] amino Moiety and the Use of These Materials in the Preparation of Water-Soluble Diphosphine Complexes of Transition Metals", *J. Org. Chem.*, vol. 46, pp. 2861-2867, 1981; XP-002237139.

Steffey, B.D et al., "Synthesis and Characterization of Palladium Complexes Containing Tridentate Ligands with PXP (X = C, N, O, S, As) Donor Sets and Their Evaluation as Electrochemical $CO_2$ Reduction Catalysts", *Organometallics*, vol. 13, pp. 4844-4855, 1994.

Cooper, T.H. et al., "Kinetic and Thermodynamic Measurements on Branched Amini Polyhiaether Ligands: A Family of Complexing Agents Analogous to EDTA and NTA Exhibiting Enhanced Selectivity for Cooper (II)", *Inorganic Chemistry*, vol. 31, pp. 1796-3804, 1992, XP-002237104, no month.

Friebe, M. et al., "Neutral '3 + 1' Mixed-ligand Oxorhenium (v) Complex with Tridentate [S,N,S] Chelates and Aminoalkanethiols: Synthesis, Characterization and Structure Determination", *Journal of the Chemical Society, Dalton Trans.*, pp. 2471-2475, 2000, XP-002237103, no month.

Konrad, M. et al., "Unsymetrically Substituted Pyrazolates: Nickel (II) Complexes of a Novel Dinucleating Ligand Providing Both N-and S-rich Co-ordination Spheres", *Journal of the Chemical Society, Dalton Trans.* pp. 199-205, 1998, XP-002237101, no month available.

Tanaka, M. et al., "Synthesis and Metal-Ion Binding Properties of Monoazathiacrown Ethers", *J. Org. Chem.* vol. 66, pp. 7008-7012, 2001. XP-002237102, no month available.

Database Crossfire Beilstein, *Beilstein Institut zur Foerferung der Chemischen Wissenchaffen*, Database accession No. 2441430, XP-002237105, Abstract, no date available.

* cited by examiner

TRIMERISATION AND OLIGOMERISATION OF OLEFINS USING A CHROMIUM BASED CATALYST

FIELD OF THE INVENTION

This invention relates to a ligand and a catalyst system, more particularly an olefin oligomerisation or trimerisation catalyst system and process.

BACKGROUND OF THE INVENTION

The oligomerisation of olefins, primarily α-olefins, with chromium catalysts has been extensively studied. More specifically, a number of chromium catalysts have been developed and used to trimerise olefins. In this regard, the trimerisation of ethylene to 1-hexene is significant since, in addition to its use as a specific chemical, 1-hexene is extensively used in polymerization processes either as a monomer or co-monomer. Furthermore, the trimeric products derived from longer chain olefins could be well utilized as synthetic lubricants (e.g. polyalphaolefins/PAOs), as well as various other applications such as components of drilling muds, and as feedstock to prepare detergents and plasticizers.

Prior art chromium based ethylene trimerisation processes include:

a) A process in which olefins are trimerised by passing the olefin in contact with a catalyst comprising the reaction product of a chromium compound, an organoaluminium compound hydrolyzed with a specific amount of water and a donor ligand selected from hydrocarbyl isonitriles, amines and ethers (U.S. Pat. No. 4,668,838);

b) A process to trimerise ethylene to 1-hexene comprising contacting ethylene with a stabilized catalyst system comprising a chromium source, a pyrrole-containing compound, a metal alkyl and an aromatic compound (European Patent No. 0 668 105);

c) A process for preparing α-olefin oligomers, which comprises carrying out oligomerisation of an α-olefin in a solvent by reacting said α-olefin with a chromium-based catalyst system comprising a combination of at least a chromium compound, an amine or metal amide, and an alkylaluminium compound, in a contacting mode that the chromium compound and the alkylaluminium compound are not previously contacted with each other (U.S. Pat. No. 5,750,817);

d) A process for oligomerising ethylene to produce 1-butene and/or 1-hexene wherein catalytic composition is obtained by mixing at least one chromium compound with at least one aryloxy aluminium compound with general formula $R_nAl(R'O)_{3-n}$ where R is a linear or branched hydrocarbyl radical containing 1 to 30 carbon atoms, R'O is an aryloxy radical containing 6 to 80 carbon atoms and n is a whole which can take the values 0, 1 or 2, and with at least one other hydrocarbyl aluminium compound selected from tris(hydocarbyl)aluminium compound or chlorinated or brominated hydrocarbyl aluminium compounds (U.S. Pat. No. 6,031,145); and e) A process for the trimerisation of ethylene, said process comprising reacting ethylene, using a catalyst comprising an aluminoxane and a polydentate phosphine, arsenic and/or antimony coordination complex of a chromium salt, such that 1-hexene is formed (U.S. Pat. No. 5,811,618).

SUMMARY OF THE INVENTION

The invention is now described in general terms with reference to the accompanying drawings.

Figure 2:
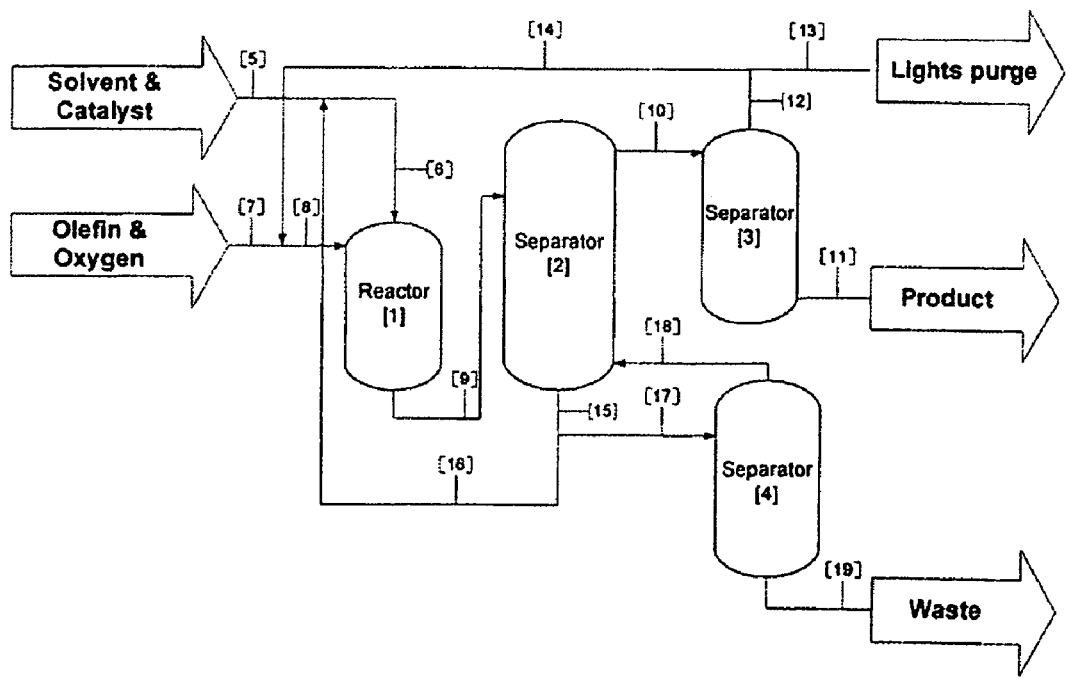

In the drawings:

FIG. 1 shows a X-Ray Crystal structure of $CrCl_3$(bis-(2-diphenylphosphino-ethyl)-amine), and FIG. 2 shows a schematic representation (flow diagram) of one embodiment of a olefin oligomerisation process, in accordance with the invention.

This invention recognizes the need for a catalyst system, which facilitates the production of 1-hexene in high selectivity while avoiding the co-production of significant quantities of polyethylene. However, the catalyst system can also be used for the trimerisation or oligomerisation of other olefins, especially α-olefins.

In this regard, it is known from the prior art (e.g. European Patent No. 537609) that chromium catalysts comprising a multidentate amine coordination complex of a chromium salt and an aluminoxane or an alkylaluminium compound are generally not particularly effective at trimerising ethylene selectively. This has also been established experimentally as is demonstrated in Example 1 below.

This invention generally relates to how the need for selectively producing 1-hexene from ethylene can be at least partly satisfied by using a chromium catalyst system containing a multidentate ligand with at least one amine functionality.

Thus, according to a first aspect of the invention there is provided a hydrocarbon conversion catalyst system, which includes: a coordination complex of a transition metal; and a mixed heteroatomic ligand having three donor heteroatoms coordinated to the transition metal, of which donor atoms at least one is nitrogen and at least two are not the same.

The ligand may be a multidentate mixed heteroatomic ligand for an oligomerisation of olefins catalyst.

The ligand may contain, in addition to nitrogen, at least one phosphorous heteroatom.

The ligand may be selected such that none of the non-carbon based heteroatoms are directly bonded to any of the other non-carbon based heteroatoms.

Typically, the ligand may not include a sulfur heteroatom.

By "multidentate mixed heteroatomic" is meant a ligand that contains more than one non-carbon based donor atoms, of which one donor atom is different from the others, and all the donor atoms are coordinated to the transition metal in the catalyst system. The applicant has found that it is important for catalyst activity that all the non-carbon based donor atoms coordinate with the transition metal and the ligand, therefore preferably, but not necessarily, needs at least one bridging atom between the donor atoms to provide the necessary distances between the donor atoms and to allow the ligand to assume the necessary spatial orientation for coordination of all donor atoms. FIG. 1 contains the molecular structure, derived from a X-Ray Crystal structure, of a complex between $CrCl_3$ and an example of such a multidentate mixed heteroatomic ligand, namely bis-(2-diphenylphosphino-ethyl)-amine. Selected bond distances and angles of this molecular structure are summarized in Table 1.

TABLE 1

Selected bond distances and angles of $CrCl_3$(bis-(2-diphenylphosphino-ethyl)-amine)

| | |
|---|---|
| Chelate bite angle | 81.08(8)° |
| | 82.07(8)° |

TABLE 1-continued

Selected bond distances and angles of CrCl₃(bis-(2-diphenylphosphino-ethyl)-amine)

| Cr—P bond distances | 2.4660(12) Å |
|---|---|
|  | 2.4678(12) Å |
| Cr—N bond distance | 2.139(3) Å |

As can be seen from FIG. 1, this specific multidentate mixed heteroatomic ligand has a meridional arrangement in the complex, thereby enabling the formation of two Cr—P bonds with nearly equal bond distances (see Table 1). Such a meridional arrangement of the ligand is only possible if there is at least one bridging atom between the donor atoms. As could be expected, the resulting P—Cr—N chelate bite angles are also very similar in size.

Therefore, the multidentate mixed heteroatomic ligand may also be selected such that none of the non-carbon based donor atoms are directly bonded to any of the other non-carbon based donor atoms.

The multidentate mixed heteroatomic ligand may be defined by the following general formula:

$R^1A(R^2BR^3R^4)(R^5CR^6R^7)$ wherein $R^1$, $R^3$, $R^4$, $R^6$ and $R^7$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^5$ are the same or different and are $C_1$ to about $C_{15}$ hydrocarbyls; and at least A, B or C is nitrogen with the remainder of A, B and C being individually nitrogen or phosphorous These multidentate mixed heteroatom based ligands can be synthesized according to procedures described in the literature or via adaptation of these, for example by A. A. Danopoulos, A. R. Wills and P. G. Edwards, *Polyhedron*, 1990, 9, 2413–2418.

Specific examples of multidentate mixed heteroatom based ligands may include bis-(2-diethylphosphino-ethyl)-amine, bis-(diethylphosphino-methyl)-amine, bis-(2-diethylphosphino-phenyl)-amine, N-methylbis-(2-diethylphosphino-ethyl)-amine, bis-(2diphenylphosphino-ethyl)-amine, (2-diethylphosphino-ethyl)(3-diethylphosphino-propyl)-amine, bis-(2-dicyclohexylphosphino-ethyl)-amine, N-benzylbis-(2-diethylphosphino-ethyl)-amine, N-methyl-(2-diethylphosphino-ethyl)(3-diethylphosphino-propyl)-amine, (2-diethylphosphino:ethyl)(2-diethylamino-ethyl)-amine, N-methyl-(2-diethylphosphino-ethyl)(2-diethylamino-ethyl)-amine and bis-(2-diethylamino-ethyl)ethylphosphine.

A suitable multidentate mixed heteroatomic ligand is bis-(2-diethylphosphino-ethyl)-amine and derivatives thereof.

The multidentate mixed heteroatomic ligands can be modified to be attached to a polymer chain (molecular wt.=1000 or higher) so that the resulting transition metal complex is soluble at elevated temperatures, but becomes insoluble at 25° C. This approach would enable the recovery of the complex from the reaction mixture for reuse and has been used for other catalyst as described by D. E. Bergbreiter et a., *J. Am. Chem. Soc.*, 1987, 109, 177–179. In a similar vain these transition metal complexes can also be immobilized by bounding the multidentate mixed heteroatomic ligands to silica, silica gel, polysiloxane or alumina backbone as demonstrated by C. Yuanyin et al., *Chinese J. React. Pol.*, 1992, 1(2), 152–159 for immobilizing platinum complexes.

According to a further aspect of the invention, there is provided an oligomerisation of olefins catalyst system.

The term "oligomerisation" generally refers to a reaction were all the monomer units of the oligomerisation product are the same. However, it may also include co-oligomerisation reactions where mixtures of olefins are used as the reagents thereby yielding products containing more than one type of monomer unit (i.e. different olefins). Such co-oligomerisation reactions often yield alkyl- and/or aryl-branched oligomeric products with distinct properties as demonstrated by C. Pelecchia et al., *Macromolecules*, 2000, 33, 2807–2814.

The hydrocarbon conversion catalyst system may include a mixed heteroatomic ligand, as described above, and a transition metal.

The transition metal may be chromium.

The catalyst system may include a combination of a mixed heteroatomic coordination complex of chromium and an aluminoxane.

The chromium coordination complexes which, upon mixing with an aluminoxane, catalyze ethylene trimerisation in accordance with the invention, may be suitably expressed by the formula $LCrX_n$ wherein X represents anions which can be the same or different, n is an integer from 0 to 5 and L is a mixed heteroatomic ligand.

The chromium precursor used in the preparation of the coordination complex may be selected from an organic or inorganic chromium compound, with the oxidation state of the chromium atom ranging from 0 to 6.

Chromium salts used in the preparation of the chromium coordination complex may be selected from chromium (III) acetylacetonate, chromium (III) acetate, chromium (III) 2,2,6,6-tetramethylheptadionate, chromium (III) tris(2-ethylhexanoate, chromium (III) chloride, chromium (II) acetate, chromium (II) chloride, chromium (II) nitrate and chromium (III) sulphate.

Alternatively, organometallic complexes, for example, chromium trichloride tris-tetrahydrofuran complex, (benzene)tricarbonyl chromium, chromium hexacarbonyl, and the like, may be used in the preparation of the chromium coordination complex.

Aluminoxanes for use in the catalyst system can be prepared as known in the art by reacting water or water containing materials with trialkylaluminium compounds. Preferred aluminoxanes are prepared from trialkylaluminium compounds such as trimethylaluminium, triethylaluminium, tripropylaluminium, tributylaluminium, triisobutylaluminium, trihexylaluminium or the like, and mixtures thereof. Mixtures of different aluminoxanes may also be used in the catalyst system. Of these, the more preferred aluminoxane is prepared from trimethylaluminium and/or triethylaluminium. The use of said aluminoxane is necessary to achieve catalytic activity.

The catalyst system may include, in addition to the aluminoxane or mixture of aluminoxanes, also a trialkylaluminium in amounts of between 0.01 to 100 mole per mole of aluminoxane. It should however be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The applicant has found that the trialylaluminium serves as a poisons scavenger to protect the aluminoxane and in some cases leads to an increase in the catalytic activity.

The aluminoxane may form part of a mixture of aluminoxanes. The applicant has found that at least a portion of the required more expensive methylaluminoxane can be replaced with a less expensive ethylaluminoxane, for example, and the resulting mixture shows the same, if not increased, catalytic activity.

The aluminoxane or mixture of aluminoxanes may preferably be selected from methylaluminoxane or ethylaluminoxane.

The chromium coordination complex and the aluminoxane may be combined in proportions to provide Al/Cr molar ratios of from about 1:1 to 10 000:1.

The hydrocarbon conversion catalyst system may be a trimerisation of α-olefins or trimerisation of ethylene catalyst system.

The hydrocarbon conversion catalyst system described in this invention may also be used in combination with another catalyst system suitable for the (polymerization of olefins. In such cases, the oligomerization or trimerisation products of the catalyst system disclosed in this invention could be incorporated into a polymer or other chemical product with desired properties. This concept of using dual catalyst systems, one for oligomerization and the other for polymerization of olefins, to manufacture polyethylene copolymers has been demonstrated before for example by G. C. Bazan, Z. J. A. Komon and X. Bu, *J. Am. Chem. Soc.*, 2000, 122, 1830 and C. Pelecchia et al., *Macromolecules*, 2000, 33, 2807–2814.

The catalyst system may be a trimerisation of α-olefins or trimerisation of ethylene catalyst system.

The multidentate mixed heteroatomic coordination complex of a chromium salt may be either added to the reaction mixture, or generated In-situ. Known literature procedures can be used for the ex-situ preparation of such coordination complexes of a chromium salt. Examples of such procedures are described by R. D Köhn and G. K. Köhn, *Angew. Chem. Int. Ed. Engl.*, 1994, 33(18), 1877–1878, R. D Köhn et al., *Angew. Chem. Int. Ed.*, 2000, 39(23), 4337–4339 and P. Wasserscheid et al., *Adv. Synth. Catal.*, 2001, 343(8), 814–818.

The catalyst of the catalyst system may be in solution in an inert solvent. These inert solvents include any saturated aliphatic and unsaturated aliphatic and aromatic hydrocarbon and halogenated hydrocarbon. The saturated aliphatic and unsaturated aliphatic hydrocarbon compound can have any number of carbon atoms per molecule, but usually contain less than 20 carbon atoms due to commercial availability and end use. Preferred solvents include, but are not limited to, benzene, toluene, xylene, ethylbenzene, mesitylene, heptane, nonane, cyclohexane, methylcyclohexane, 1-hexene, chlorobenzene, anisole and the like.

The individual components of the catalyst system described in this disclosure may be combined simultaneously or sequentially in any order, and in the presence or absence of a solvent, in order to give an active catalyst. The mixing of the catalyst components can be conducted at any temperature between 0° C. and 150° C. The temperature during the mixing of the catalyst components does not seem to have a significant effect on the catalyst performance. The presence of an olefin during the mixing of the catalyst components generally provides a protective effect which may result in improved catalyst performance.

The chromium coordination complex and the aluminoxane are combined in proportions to provide Al/Cr molar ratios of from about 1:1 to 10 000:1, and 30 preferably, from about 1:1 to 1000:1.

The catalyst system, or its individual components, may also be immobilized by supporting it on a heterogeneous surface such as silica, alumina, silica-alumina, MgO, zirconia or the like. This approach would also facilitate the recovery of the catalyst from the reaction mixture for reuse. The concept was successfully demonstrated with another chromium-based ethylene trimerisation catalyst by T. Monoi and Y. Sasaki, *J. Mol. Cat.A:Chem.*, 1987,109, 177–179. In some cases, the heterogeneous surface (support) can also act as a catalyst component, for example where such supports contain aluminoxane functionalities or where the support is capable of performing similar chemical functions as an aluminoxane, which is for instance the case with IOLA™ (a commercial product from Davison Catalysts).

According to a further aspect there is provided a process for the oligomerisation of olefins, the process including the step of contacting the olefins at pressures from atmospheric to 100 barg and at temperatures of from 0° C. to 200° C., with a catalyst system as described above.

The process of this invention may also be carried out in an inert solvent. Any inert solvent that does not react with trialkylaluminium and aluminoxane compounds can be used. These inert solvents include any saturated aliphatic and unsaturated aliphatic and aromatic hydrocarbon and halogenated hydrocarbon. Preferred solvents include, but are not limited to, benzene, toluene, xylene, heptane, cyclohexane, 1-hexene and the like. The amount of solvent is not exceptionally critical and generally ranges from about 50 to 99.9 wt % of the initial reaction mixture. Nevertheless, since the catalyst productivity tends to be somewhat higher at fairly low catalyst concentrations in the initial reaction mixture (typically in the range of 0.001–0.1 mmol Cr/100 ml reaction mixture), the catalyst concentration is chosen such that the catalyst productivity and selectivity is maximized.

The catalyst is dissolved in an inert solvent.

The process may include the step of generating the multidentate mixed heteroatomic complex of chromium in-situ in a reaction mixture.

The process of this invention may be carried at pressures from atmospheric to 100 barg. Generally the process can be performed at any pressure within this range, but here again the actual reaction pressure is chosen such that the catalyst productivity and selectivity is maximized. Ethylene pressures in the range of 30–60 bar are particularly preferred.

The process of this invention may be carried out at temperatures from 0° C. to 200° C. The process can normally be conducted at any temperature within this range, but as is the case with the ethylene pressure, the actual reaction temperature is chosen such that the catalyst productivity and selectivity is maximized. Temperatures in the range of 80–120° C. are particularly preferred.

The process may be carried out in the presence of an oxidizing agent such as oxygen or the like.

The process can normally be conducted at any temperature within this range, but as is the case with the ethylene pressure, the actual reaction temperature is chosen such that the catalyst productivity and selectivity is maximized. Temperatures in the range of 80–120° C. are particularly preferred.

The process may be carried out in the presence of an oxidizing agent such as oxygen or the like. In this respect it was found that the use of olefin reagents, such as ethylene, containing low quantities of oxygen (1–2000 parts per million) resulted in improvements in the performance of the catalyst system as well as in the product selectivity.

Although the catalyst, its individual components, reagents, solvents and reaction products are generally employed on a once-through basis, any of these materials can, and are indeed preferred to, be recycled to some extent in order to minimize production costs.

This process may comprise, in combination a) a reactor, b) at least one inlet line into this reactor for olefin reactant and the catalyst system, c) effluent lines from this reactor for oligomerisation reaction products, and d) at least one separator to separate the desired oligomerisation reaction products, wherein the catalyst system may include a multidentate mixed heteroatomic coordination complex of a chromium salt and an aluminoxane.

FIG. 2 is a schematic representation (flow diagram) of one embodiment of this olefin oligomerisation process using three separators to separate the reaction products, solvent and spent catalyst (waste). While this drawing describes one embodiment of the invention for the purpose of illustration, the invention is not to be construed as limited by this schematic flow diagram, but the drawing is rather intended to cover all changes and modifications within the spirit and scope thereof.

Various additional pumps, valves, heaters, coolers and other conventional equipment necessary for the practice of this invention will be familiar to one skilled in the art. This additional equipment has been omitted from FIG. 2 for the sake of clarity.

The following description of the flow diagram provides one method of operating the process, in accordance with the invention, and aims to give a further understanding of the aspects of this invention. As used in the description, "reactor effluent" refers to all components that can be removed from an oligomerisation reactor, including, but not limited to, unreacted olefin, catalyst system, oligomerisation product(s) and co-product(s). "Waste" refers to reaction co-product(s) with a higher molecular mass than the desired oligomerisation reaction product, polymeric products and the used catalyst system. "Product" refers to product(s) of the olefin oligomerisation reaction.

Olefin, and optionally oxygen or air, is fed trough inlet line 7/8 into the oligomerisation reactor 1. Inlet line 5/6 introduces the catalyst system and optionally, solvent, into the oligomerisation reactor 1. Reactor effluent is removed from reactor 1 via line 9. It should be noted that lines 6, 8 and 9 can be located anywhere on the reactor 1. It is preferable that the contents in lines 9, 15,16,17 and 19 is maintained at a higher temperature in order to keep undesirable polymer particles from precipitating. The formation of such particles may have a detrimental effect on the operation of this process.

Line 9 introduces reactor effluent into separator 2 that separates unreacted olefin and reaction product(s) from higher boiling solvent(s), reaction product(s) and the used catalyst system. Lines 15/16 is an optional embodiment of the invention and can be used to facilitate the return of the higher boiling compounds in the reactor effluent, including the catalyst system, to reactor 1 via inlet line 6. Line 15/17 transports an effluent stream, comprising higher boiling compounds and used catalyst system, from separator 2 to separator 4, which separates the solvent from all other compounds in this effluent stream. Line 18 is used to return the solvent to separator 2. Line 19 is an effluent line that transports waste from separator 4. Line 10 transports effluent comprising unreacted olefin and the major reaction product(s) from separator 2 to separator 3, that separates the unreacted olefin from the major reaction product(s).

Line 12/14 contains effluent comprising unreacted olefin and small quantities of very light boiling reaction product(s), e.g. 1-butene, and facilitates the recovery of the olefinic reagent by transporting it back to inlet line 6. Line 12/14 is a purge line containing unreacted olefin and small quantities of very light boiling reaction product(s) that is used to prevent a build up of very light boiling reaction product(s). Line 11 is an effluent line containing the major reaction product(s).

In another embodiment of the process the reactor and a separator may be combined to facilitate the simultaneous formation of reaction products and separation of these compounds from the reactor. This process principle is commonly known as reactive distillation when the reaction is a homogeneous liquid phase reaction. When the catalyst system exhibits no solubility in the solvent or reaction products, and is fixed in the reactor so that it does not exit the to reactor with the reactor product, solvent and unreacted olefin, the process principle is commonly known as catalytic distillation.

The oligomerisation process described herein may be used in a process in which trimerisation and polymerization of ethylene occur simultaneously leading to the incorporation of the trimerisation products into a copolymer. One example of this type of process is described in U.S. Pat. No. 5,786,431.

EXAMPLES OF PERFORMING THE INVENTION

The invention will now be described with reference to the following examples which are not in any way intended to limit the scope of the invention.

In the examples that follow all procedures were carried out under inert conditions, using pre-dried reagents.

Example 1

Reaction of $CrCl_3$(pentamethyidletylenetriamine)/ MAO with ethylene

The reaction was conducted in a 75 ml stainless steel autoclave equipped with an addition funnel, gas inlet valve and a magnetic stirrer bar. The addition funnel was charged with 0.0149 g (0.0449 mmol) of $CrCl_3$(pentamethyldietyle-netriamine) dissolved in 20 ml of toluene and to the base of the autoclave was added 9.0 ml of 1.5M MAO solution in toluene. Over 20 minutes the base of the autoclave was heated to 100° C., after which time the reactor was charged with ethylene to a pressure of 40 bar and the addition funnel was opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by gas-chromatography (GC). The liquid contained in the autoclave was quenched with ethanol followed by 10% hydrochloric acid, and 1.000 ml of nonane was added as a GC internal standard. The liquid/internal standard mixture was also analysed by GC. Both GC analyses indicated that 0.12 g oligomers were formed of which 0.0048 g (4 mass %) were hexenes. Filtration of the liquids gave 0.12 g of polyethylene.

Example 2

Preparation of CrCl$_3$(bis-(2-diphenylphosphinoethyl)-amine)

CrCl$_3$(THF)$_3$ (0.907 mmol) was suspended in 6 ml THF (tetrahydrofuran) and a 3 ml THF solution of bis-(2-diphenylphosphino-ethyl)-amine (0.934 mmol) added. Approximately one halve of the solvent was removed by vacuum distillation before 10 mL of diethylether was added. The solid product was collected by filtration and washed with 10 mL diethylether. After drying under vacuum, 0.342 g CrCl$_3$ (bis-(2-diphenylphosphino-ethyl)-amine) was obtained as a purple solid, (Yield: 92% based on CrCl3(THF)$_3$). +FAB data: m/z 598 [M]$^+$, 563 [M—Cl]$^+$. Elemental analysis: Calculated for C$_{28}$H$_{29}$P$_2$NCl$_3$Cr (found): C 56.07 (55.84), N 2.34 (2.14) and H 4.87 (5.16). Crystal data: DMSO, C$_{30}$H$_{35}$Cl$_3$CrNOP$_2$S, M=653.92, monoclinic, a=27.667(7), b=14.751(4), c=16.512(4) Å, β=100.923(7) °, U=6617(3) Å$^3$, T=293(2) K, space group C2/c (no. 15), Z=8, μ (Mo—K$_α$)=0.769 mm$^{-1}$, 28626 reflections measured, 6532 unique (R$_{int}$=0.0662) which were used in all calculations. The final R(F) and wR(F$^2$) were 0.0521 (I>2σ(I) and 0.1512 (all data), respectively. Selected bond distances (Å) and angles (°): Cr—P1 2.4660(12), Cr—P2 2.4678(12), Cr—N 2.139(3), Cr—Cl1 2.2934(11), Cr—Cl2 2.3081(11), Cr—Cl3 2.3480(11), N—Cr—P1 81.08(8), N—Cr—P2 82.07(8), P1-Cr—P2 163.10(4), N—Cr—Cl1 176.74(8), N—Cr—Cl2 87.59(8) and N—Cr—Cl3 85.00(8).

Example 3

Ethylene trimerisation using CrCl$_3$(bis-(2-diphenylphosphino-ethyl)-amine)/MAO Catalysis was conducted in a 75 ml stainless steel autoclave equipped with an addition funnel, gas inlet valve and a magnetic stirrer bar. The addition funnel was charged with 0.0241 g (0.0402 mmol) of CrCl$_3$(bis-(2-diphenylphosphino-ethyl)-amine) dissolved in 20 ml of toluene and to the base of the autoclave was added 3.3 ml of 1.5M MAO solution in toluene. Over 20 minutes the base of the autoclave was heated to 100° C., after which time the reactor was charged with ethylene to a pressure of 40 bar and the addition funnel was opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by gas-chromatography (GC). The liquid contained in the autoclave was quenched with ethanol followed by 10% hydrochloric acid, and 1.000 ml of nonane was added as a GC internal standard. The top layer of organics was analysed by GC and found to contain 0.08 g butenes, 4.75 g 1-hexene and 0.04 g other hexene isomers. The gas phase was found to contain 0.01 g of butene. Filtration of the liquids gave 0.007 g of polyethylene.

Example 4

Ethylene trimerisation using CrCl$_3$(bis-(2-diphenylphosphino-ethyl)-amine)/MAO The procedure of example 3 was repeated but using 0.0066 g (0.011 mmol) of CrCl$_3$(bis-(2-diphenylphosphino-ethyl)-amine) and 5.0 mL of 1.5M MAO solution. The reaction yielded 2.72 g products containing 0.28 g polyethylene, 2.23 g 1-hexene and 0.02 g other hexene isomers.

Example 5

Preparation of bis(2diethylphosphinoethyl)-amine i) Preparation of (2-chloroethyl)-trimethylsilylamine

Bis(2-chloroethyl)amine hydrochloride (50 g, 0.28 mol) was suspended in a mixture of triethylamine (500 ml), Me$_3$SiCl (171 g, 1.58 mol) and (CH$_3$)$_2$SO (1.25 ml). The resulting mixture was stirred at room temperature for 2 hours, after which it was heated under reflux for 16 hours. After cooling to room temperature, the off-white suspension was filtered, the solvent removed in vacuo and the product filtered again to give 31.93 g of a colourless oil (Yield: 53.5%).

ii) Preparation of bis(2-diethylphosphino-ethyl)-amine

To a stirred solution of diethylphosphine (6.72 g, 74,6 mmol) in THF (150 ml) at −35° C., was added 47 ml of n-BuLi (1.6 M). Next, bis(2-chloroethyl)trimethylsilylamine (8.18 g, 38.4 mmol) in 40 ml tetrahydrofuran was then added dropwise to the LiP(Et)$_2$ in tetrahydrofuran at −50° C. The mixture was allowed to warm to room temperature and stirred for 30 minutes. It was then heated to 60° C. and stirred overnight after which 100 ml of water was added to hydrolyse the silyl groups and the reaction mixture heated to 60° C. for 1 hour to ensure complete removal of the silyl groups. The reaction mixture was dried by passing it through a small bed of MgSO$_4$, which was subsequently washed through with 60 ml diethyl ether. The solvent was removed to give 6.96 g bis(2-diethylphosphino-ethyl)-amine (Yield: 73%). $^1$H-NMR (C$_6$D$_6$) δ 1.12 (12H, d of t, CH$_2$CH$_3$, J=7.2 and 14.1 Hz), 1.38 (8H, q, CH$_2$CH$_3$, J=7.2), 1.60 (4H, t, (CH$_2$)P, J=7.2) and 2.84 (4H, q, (CH$_2$)N, J=7.8). $^{31}$P-NMR (C$_6$D$_6$) δ −26.02.

Example 6

Preparation of CrCl$_3$(bis(2-diethylphosphino-ethyl)-amine)

A solution of bis(2-diethylphosphino-ethyl)-amine (0.183 g 0.734 mmol) in 5 ml THF was added to a solution of CrCl$_3$(THF)$_3$ (0.262 g, 0.699 mmol) in 10 ml THF at room temperature. The solution was stirred for 10 minutes after which the solvent was removed in vacuo until about 3 ml remained. The solution was filtered, washed with additional diethyl ether and dried in vacuo to give 0.254 g of the product (Yield: 89%). Elemental analysis: Calculated for C$_{12}$H$_{29}$NP$_2$Cl$_3$Cr (found) C 35.36 (35.29), N 3.44 (3.21) and H 7.17 (7.49).

Example 7

Ethylene trimerisation using CrCl$_3$(bis-(2-diethylphosphino-ethyl)-amine)/MAO Catalysis was conducted in a 75 ml stainless steel autoclave equipped with an addition funnel, gas inlet valve and a magnetic stirrer bar. The addition funnel was charged with 0.0044 g (0.0108 mmol) of CrCl$_3$(bis-(2-diethylphosphino-ethyl)-amine) dissolved in 20 ml of toluene and to the base of the autoclave was added 5 ml of 1.5M MAO solution in toluene. Over 20 minutes the base of the autoclave was heated to 100° C., after which time the reactor was charged with ethylene to a pressure of 40 bar and the addition funnel was opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by gas-chromatography (GC). The liquid contained in the autoclave was quenched with ethanol followed by 10% hydrochloric acid, and 1.000 ml of nonane was added as a GC internal standard. The reaction yielded 0.063 g polyethylene, 0.04 g butene, 8.67 g 1-hexene and 0.10 g other hexene isomers.

Example 8

Ethylene trimerisation using CrCl$_3$(bis-(2-diethylphosphino-ethyl)-amine)/MAO

The procedure of example 7 was repeated but using 0.0048 g (0.0118 mmol) of CrCl$_3$(bis-(2-diethylphosphino-ethyl)amine) and a reaction temperature of 80° C. for 1 hour. The reaction yielded 0.045 g polyethylene, 0.21 g butene, 12.77 g 1-hexene, 0.09 g other hexene isomers and 0.09 g decenes.

Example 9

Ethylene trimerisation using CrCl$_3$(bis-(2-diethylphosphino-ethyl)-amine)/MAO

The procedure of example 7 was repeated but using 0.0052 g (0.013 mmol) of CrCl$_3$(bis-(2-diethylphosphinoethyl)amine) and a reaction temperature of 50° C. for 1 hour. The reaction yielded 0.54 g products containing 0.12 g polyethylene, 0.41 g 1-hexene, 0.01 g other hexene isomers.

Example 10

Ethylene trimerisation using CrCl$_3$(bis-(2-diethylphosphino-ethyl)-amine)/MAO

The procedure of example 7 was repeated but using 0.0046 g (0.0113 mmol) of CrCl$_3$(bis-(2-diethylphosphino-ethyl)amine) and a reaction temperature of 120° C. The reaction yielded 7.86 g products containing 0.16 g polyethylene, 7.26 g 1-hexene, 0.05 g other hexene isomers.

Example 11

Ethylene trimerisation using CrCl$_3$(bis-(2diethylphosphino-ethyl)-amine)/MAO

The procedure of example 7 was repeated but using 0.020 g (0.05 mmol) of CrCl$_3$(bis-(2-diethylphosphinoethyl)amine) and 3.3 ml of 1.5M MAO solution in toluene. The reaction yielded 12.13 g products containing 0.24 g polyethylene, 11.79 g 1-hexene, 0.10 g other hexene isomers.

The invention claimed is:

1. A hydrocarbon conversion catalyst system, comprising a coordination complex of a transition metal; and a mixed heteroatomic ligand having three donor heteroatoms coordinated to the transition metal, wherein, among the donor heteroatoms, at least one is nitrogen and at least two are not the same.

2. A catalyst system as claimed in claim 1, wherein one of the donor heteroatoms is phosphorous.

3. A catalyst system as claimed in claim 1, wherein the ligand is selected such that none of the donor heteroatoms are directly bonded to any of the other donor atoms.

4. A catalyst system as claimed in claim 3, wherein the ligand is described by the general formula R$^1$A(R$^2$BR$^3$R$^4$)(R$^5$CR$^6$R$^7$) wherein R$^1$, R$^3$, R$^4$, R$^6$ and R$^7$ may be hydrogen or independently be a substituent selected from alkyl, aryl, aryloxy, halogen, nitro, alkoxycarbonyl, carbonyloxy, alkoxy, aminocarbonyl, carbonylamino, dialkylamino, derivatives thereof, and aryl substituted with any of these substituents; R$^2$ and R$^5$ are the same or different and are C$_1$ to about C$_{15}$ hydrocarbyls; and at least A, B or C is nitrogen with the remainder of A, B and C being individually nitrogen or phosphorous.

5. A catalyst system as claimed in claim 4, wherein the ligand is selected from bis-(2-diethylphosphino-ethyl)-amine, N-methylbis-(2-diethylphosphino-ethyl)-amine, bis-(2-diphenylphosphino-ethyl)-amine, bis-(diethylphosphino-methyl)-amine, bis-(2-diethylphosphino-phenyl)-amine, (2-diethylphosphino-ethyl)(3-diethylphosphino-propyl)-amine, bis-(2-dicyclohexylphosphino-ethyl)-amine, N-benzylbis-(2-diethylphosphino-ethyl)-amine, N-methyl-(2-diethylphosphino-ethyl)(3-diethylphosphino-propyl)-amine, (2-diethylphosphino-ethyl)(2-diethylamino-ethyl)-amine, N-methyl-(2-diethylphosphino-ethyl)(2-diethylamino-ethyl)-amine, bis-(2-diethylamino-ethyl)ethylphosphine, and derivatives thereof.

6. A catalyst system as claimed in claim 1, wherein the catalyst system is a trimerisation of α-olefins catalyst system.

7. A catalyst system as claimed in claim 1, wherein the catalyst system is a trimerisation of ethylene to 1-hexene catalyst system.

8. A catalyst system as claimed in claim 1, wherein the transition metal is chromium.

9. A catalyst system as claimed in claim 8, further comprising an aluminoxane.

10. A catalyst system as claimed in claim 8, further comprising a mixture of aluminoxanes.

11. A catalyst system as claimed in claim 10, wherein the coordination complex and the heteroatomic ligand form a mixed heteroatomic coordination complex expressed by the formula LCrX$_n$, wherein X represents anions which can be the same or different, n is an integer from 0 to 5, and L is a mixed heteroatomic ligand.

12. A catalyst system as claimed in claim 9, wherein the coordination complex is an organic or inorganic chromium compound with the oxidation state of the chromium atom ranging from 0 to 6.

13. A catalyst system as claimed in claim 9, wherein the coordination complex is selected from chromium (III) acetylacetonate, chromium (III) acetate, chromium (III) 2,2,6,6-tetramethylheptadionate, chromium (III) tris(2-ethylhexanoate), chromium (III) chloride, chromium (II) acetate, chromium (II) chloride, chromium (II) nitrates and chromium (III) sulphate.

14. A catalyst system as claimed in claim 9, wherein the aluminoxane is prepared from a trialkylaluminium.

15. A catalyst system as claimed in claim 9, further comprising a trialkylaluminium.

16. A catalyst system as claimed in claim 9, wherein the aluminoxane is methylaluminoxane or ethylaluminoxane.

17. A process for the oligomerisation of olefins, the process including the step of contacting the olefins at pressure from atmospheric to 101 atm and at temperature from 0° C. to 200° C., with a catalyst system as claimed in claim 1.

18. A process as claimed in claim 17, wherein the olefins are contacted with the catalyst system at pressure from 31–51 atm and at temperature from 80° C. to 100° C.

19. A process as claimed in claim 17, further comprising the step of dissolving the catalyst system in an inert solvent before the contacting step.

20. A process as claimed in claim 18, further comprising the step of generating a multidentate mixed heteroatomic complex of a chromium salt in-situ before the contacting step.

21. A catalyst system as claimed in claim 4, wherein the catalyst system is a trimerisation of α-olefins catalyst system.

22. A catalyst system as claimed in claim 4, wherein the transition metal is chromium.

23. A catalyst system as claimed in claim 22, further comprising an aluminoxane.

24. A catalyst system as claimed in claim 22, further comprising a mixture of aluminoxanes.

25. A catalyst system as claimed in claim 24, wherein the coordination complex and the heteroatomic ligand form a mixed heteroatomic coordination complex expressed by the formula $LCrX_n$, wherein X represents anions which can be the same or different, n is an integer from 0 to 5, and L is a mixed heteroatomic ligand.

26. A catalyst system as claimed in claim 23, wherein the coordination complex is selected from chromium(III)acetylacetonate, chromium (III) acetate, chromium (III) 2,2,6,6-tetramethylheptadionate, chromium (III) tris(2-ethylhexanoate), chromium (III) chloride, chromium (II) acetate, chromium (II) chloride, chromium (II) nitrate, and chromium (III) sulphate.

27. A process for the oligomerisation of olefins, the process including the step of contacting the olefins at pressure from atmospheric to 101 atm and at temperature from 0° C. to 200° C., with a catalyst system as claimed in claim 4.

28. A process as claimed in claim 27, wherein the olefins are contacted with the catalyst system at pressure from 31-51 atm and at temperature from 80° C. to 100° C.

29. A process as claimed in claim 28, further comprising the step of dissolving the catalyst system in an inert solvent before the contacting step.

30. A process as claimed in claim 29, further comprising the step of generating a multidentate mixed heteroatomic complex of a chromium salt in-situ before the contacting step.

* * * * *